United States Patent [19]

Pallos et al.

[11] 4,197,111
[45] Apr. 8, 1980

[54] 1,8-NAPHTHALIMIDES AND HERBICIDE ANTIDOTES

[75] Inventors: Ferenc M. Pallos, Walnut Creek, Calif.; Duane R. Arneklev, Plentywood, Mont.

[73] Assignee: Stauffer Chemical Company, Westport, Conn.

[21] Appl. No.: 946,243

[22] Filed: Sep. 27, 1978

[51] Int. Cl.² ............................................. A01N 9/22
[52] U.S. Cl. .......................................... 71/88; 71/94; 71/90; 71/92; 71/100
[58] Field of Search .................. 71/94, 88, 100, 92, 71/90

[56] References Cited

U.S. PATENT DOCUMENTS

| | | | |
|---|---|---|---|
| 3,131,509 | 5/1964 | Hoffmann | 71/111 X |
| 3,564,768 | 2/1971 | Hoffman | 71/100 X |
| 3,702,759 | 11/1972 | Hoffmann | 71/77 |
| 3,719,466 | 3/1973 | Ahle | 71/88 |
| 3,749,566 | 7/1973 | Hoffmann | 71/100 |

*Primary Examiner*—Catherine L. Mills
*Attorney, Agent, or Firm*—Harry A. Pacini

[57] ABSTRACT

Rice is protected from herbicidal injury due to thiolcarbamate herbicides using certain 1,8-naphthalimides as a herbicide antidote. The 1,8-naphthalimides have the formula

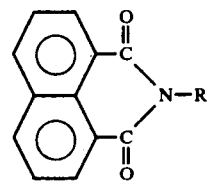

where R is selected from the group consisting of alkyl containing 5–20 carbon atoms, inclusive, hydroxyalkyl and lower alkoxyalkyl, benzyl, chloroacetamido, halophenylureido, thiazolyl, benzimidazolyl and halo substituted benzimidazolyl.

52 Claims, No Drawings

1,8-NAPHTHALIMIDES AND HERBICIDE ANTIDOTES

FIELD OF THE INVENTION

This invention relates to the use of certain 1,8-naphthalimides to protect rice from herbicidal injury.

DESCRIPTION OF THE PRIOR ART

In U.S. Pat. No. 3,564,768, Feb. 23, 1971, to Otto L. Hoffman, it is disclosed that corn is protected from injury by N,N-dialkylthiolcarbamate ester pre-emergent herbicides by coating the corn seeds prior to planting with a non-phytotoxic quantity of a bifunctional compound selected from the group consisting of 1,8-naphthalic anhydride, lower alkyl 1,8-naphthalate esters, N,N-diallyl-1,8-naphthalic acid, propynylamine salts of strong inorganic acids, N,N'-diallyl-oxamide, N,N'-dipropynyloxamide, N,N,N',N'-tetrapropynyloxamide and N,N'-dipropynylmaloamide.

In another patent, U.S. Pat. No. 3,702,759, November 14, 1972, Otto L. Hoffman teaches that corn is protected from injury by N,N-dialkylthiolcarbamate ester pre-emergent herbicides, and also other herbicides such as 3-amino-2,4-dichlorobenzoic acid and 2-chloro-2',6'-diethyl-N-(methoxymethyl)-acetanilide by coating the corn seeds prior to planting with 1,8-naphthalic anhydride, the free acid or lower alkyl naphthalate esters of naphthalate salts in combination with S-(2-propynyl) thiosemicarbazide.

In U.S. Pat. No. 3,719,466, Mar. 6, 1973, James Ahle teaches that grain is protected from injury by 2-chloro-2',6'-diethyl-N-(methoxymethyl) acetanilide by coating the seeds with one of a small group of specific compounds. For example, grain sorghum seed may be coated with a compound selected from ethyl-2-perimidine-carboxylate, N,N-diallylpropionamide, N,N-diallylacetamide, 1,8-didecylnaphthalate, 1,8-disodium naphthalate and 1,8-naphthalic acid and wheat is protected by coating the seeds with ethyl N,N-di-2-propynyloxamate and/or ethyl, N,N-diallyl-oxamate.

In U.S. Pat. No. 3,749,566, July 31, 1973, to Otto L. Hoffman, rice seed is rendered resistent to N,N-dialkyl thiolcarbamate ester pre-emergence herbicides by soaking the rice seed in an aqueous solution of an amine salt obtained by the addition of an amine and water to 1,8-naphthalic anhydride or 1,8-naphthalic acid.

DETAILED DESCRIPTION OF THE INVENTION

It has now been discovered that rice can be protected from injury due to a thiolcarbamate herbicide by applying certain 1,8-naphthalimides. Accordingly, this invention comprises a method of protecting rice from injury due to a thiolcarbamate herbicide by applying to the soil in which a herbicidally effective amount of said thiolcarbamate is used, an antidotally effective amount of a 1,8-naphthalimide having the formula

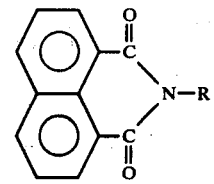

wherein R is selected from the group consisting of alkyl containing 5-20 carbon atoms, inclusive; hydroxyalkyl containing 1-6 carbon atoms, inclusive, and lower alkoxyalkyl containing 2-12 carbon atoms, inclusive; benzyl; chloroacetamido; halophenylureido, in which halo is 1-4 chloro, bromo or fluoro; thiazolyl; benzimidazolyl and halo substituted benzimidazolyl, in which halo is 1-3 chloro, bromo or fluoro.

The term herbicide refers to a compound that selectively controls, prevents, or inhibits the growth of vegetation or plants. Herbicides are generally applied to the soil where control of undesired vegetation is sought. In agricultural use, the herbicide can be applied to the soil before, after, or simultaneously with planting of the crop seeds.

The amount of herbicide employed in a given situation will depend on the particular herbicide used, the crop to be grown in the field, the types of weeds to be controlled and the degree of control desired. It is often advantageous to use a mixture of herbicides to obtain optimum control of a broad spectrum of weed species. At times, the rate of application of herbicide required to achieve the desired degree of control reresults in injury to the crop. For example, rice may be injured by the application of thiolcarbamate herbicides when they are applied in a herbicidally effective amount to control undesired weeds. Thiolcarbamate herbicidal compounds include, for example, S-ethyl N,N-di-n-propyl thiolcarbamate, ethyl N-cyclohexyl-N-ethyl thiolcarbamate, S-n-propyl, N,N-di-n-propyl thiolcarbamate, S-ethyl N,N-diisobutyl thiolcarbamate, S-ethyl hexahydro-1H-azepine carbothioate, 2,3,3-trichloroallyl N,N-diisopropyl thiolcarbamate, S-n-propyl N-n-butyl-N-ethyl thiolcarbamate, S-isopropyl-1-(5-phenyl-2-methylpiperidine) carbothioate, S-isopropyl hexahydro-1H-azepine carbothioate and S-4-chlorobenzyl diethyl thiolcarbamate.

The term herbicide antidote refers to a compound which, when applied to the crop seed or the soil in which the crop seed is or will be planted, counteracts the growth controlling injurious effect of the herbicide on the crop. The term antidotally effective amount refers to the amount of the antidote which when applied to the crop seed or soil achieves the desired protection of the crop. This amount will vary widely, depending on the particular herbicide or mixtures of herbicides used and the method of application of the antidote. One skilled in the art, with the teaching of this specification before him, will be able, without undue experimentation, to determine the antidotally effective amount of the selected 1,8-naphthalimide used can range from about 0.5 to about 30 pounds per acre. A rate of application of about 1 to about 10 pounds per acre is preferred.

In general, the amount of antidote compound used in proportion to the amount of herbicide used, will be from about 0.001 to about 30, preferably about 0.01 to about 20 parts by weight of antidote per part herbicide.

The 1,8-naphthalimides used in accordance with this invention are known compounds. These compounds can be prepared by the reaction of N-amino-1,8-naphthalimide and an appropriate substituted isocyanate or alkanoyl chloride in the presence of a catalyst, such as triethylamine and dibutyltinlaurate. Also the compounds are prepared by the reaction of 1,8-naphthalic anhydride and an appropriate primary amine such as n-heptylamine and the like. A solvent is preferred in each of the above-described reactions to facilitate the reaction and processing. Work up of the reaction product is by normal procedures of filtration, distillation or crystalization as required. Characterization of the product is accomplished by the usual analytical means, such as infrared spectroscopy and nuclear magnetic resonance.

The following examples illustrate in detail the preparation of the 1,8-naphthalimides of this invention.

EXAMPLE I

Preparation of
N-(N'-4-chlorophenyl)ureido-1,8-naphthalimide

Seven and one-tenth grams (0.033 mole) of N-amino-1,8-naphthalimide was dissolved in 300 milliliters (ml.) of refluxing dioxane. To this solution was added 5.1 grams (0.033 mole) of p-chlorophenyl-isocyanate. Three drops of triethylamine and one drop of dibutyltindilaurate were added to the reaction mixture while at below refluxing temperature. This was stirred at 65° C. overnight, cooled and the resulting solid filtered off and dried. There was obtained 7.7 grams of the title compound, m.p. 305°–310° C. Structure was confirmed by infrared and nuclear magnetic resonance.

EXAMPLE II

Preparation of N-n-heptyl-1,8-naphthalimide

To 9.9 grams (0.05 mole) of 1,8-naphthalic anhydride suspended in 150 ml. of toluene was added 5.8 grams (0.05 mole) n-heptylamine. The reaction mixture was refluxed for 3 hours. Then the reaction mixture was stirred overnight at room temperature. Any solid material was filtered off and discarded and the remaining liquid was evporated to dryness. There was obtained 13.8 grams of the title compound, m.p. 63°–67° C. The structure was confirmed by infrared and nuclear magnetic resonance.

EXAMPLE III

Preparation of N-Chloroacetamido-1,8-naphthalimide

To 5.3 grams (0.25 mole) of N-amino-1,8-naphthalimide in 150 ml. of benzene was added 2.5 grams triethylamine. Three and seven-tenths grams (0.025 mole) of chloroacetyl chloride in 50 ml. of benzene was added dropwise. The temperature went up to about 30° C. After addition was completed, the reaction mixture was refluxed for 2 hours and then allowed to stir overnight at room temperature. Water was added, stirred, and the resulting solid material filtered, washed and dried. There was obtained 2.3 grams of the title compound, m.p. 139°–144° C. The structure was confirmed by infrared and nuclear magnetic resonance.

EXAMPLE IV

Preparation of
N-(2')-Benzimidazolyl-1,8-naphthalimide

Five grams (0.025 mole) of 1,8-naphthalic anhydride and 3.4 grams (0.025 mole) of 2-aminobenzimidazole in 75 ml. toluene were refluxed for 6 hours and allowed to stir at room temperature overnight. The resulting solid was filtered off and dried. There was obtained 7.8 grams of the title compound, m.p. 349°–356° C. The structure was confirmed by infrared and nuclear magnetic resonance.

Other naphthalimides, typical of those useful as antidotes to protect rice from injury from thiolcarbamate herbicides are listed in Table I. Compounds, including those prepared in the above examples, are assigned compound numbers in Table I. The compound numbers are then used throughout the remainder of the specification.

TABLE I

| Compound No. | R | Physical Constant |
|---|---|---|
| 1 | -i-$C_5H_9$ | m.p. 90°–94° C. |
| 2* | -n-$C_7H_{15}$ | m.p. 63°–67° C. |
| 3 | -n-$C_8H_{17}$ | $n_D^{30}$ 1.5884 |
| 4 | -n-$C_{10}H_{21}$ | m.p. 47°–50° C. |
| 5 | -n-$C_{11}H_{23}$ | m.p. 46°–48° C. |
| 6 | -n-$C_{16}H_{33}$ | m.p. 58°–61° C. |
| 7 | —$CH_2CH_2OH$ | m.p. 171°–174° C. |
| 8 | —$CH_2CH(OC_2H_5)_2$ | m.p. 94°–97° C. |
| 9* | —NHCCH$_2$Cl (C=O) | m.p. 136°–144° C. |
| 10* | —NHCNH—(C$_6H_4$)—Cl (C=O) | m.p. 305°–310° C. |
| 11 | —$CH_2$—(C$_6H_5$) | m.p. 195°–199° C. |
| 12 | benzothiazolyl | m.p. 254°–260° C. |
| 13* | benzimidazolyl | m.p. 349°–356° C. |
| 14 | chloro-benzimidazolyl | m.p. 304°–308° C. |

*Compound Number 2 is Example II
*Compound Number 9 is Example III
*Compound Number 10 is Example I
*Compound Number 13 is Example IV These compounds were evaluated as antidotes to protect rice from injury due to the herbicide S-ethyl hexahydro-1H-azepine carbothioate using the following evaluation procedure.

In-Furrow Evaluation (IF)

Stock solutions of the herbicide and each antidote compound were prepared as follows:

HERBICIDE

S-ethyl hexahydro-1H-azepine carbothioate (OR-DRAM®6E) 738 milligrams (mg.) is dissolved in 120 ml. water such that 4 ml. applied to a flat is equivalent to 4.5 lb/A PPI.

ANTIDOTE 95 mg. of each antidote compound to be tested was dissolved in 15 ml. of acetone containing 1% Tween 20®(polyoxyethylene sorbitan monolaurate) so that 1.5 ml. when atomized during the in-furrow method described below, is equivalent to 5 pounds per acre.

Small flats were filled with Felton loamy sand soil. The soil from each flat was transferred to a five-gallon cement mixer and 4 ml. of herbicide stock solution was added. After the herbicide incorporation the soil was placed back into the flats with the exception of about one pint of soil which was reserved for later use to cover the seeds after planting.

Rows ¼-inch deep were made lengthwise in each treated flat and seeds were placed in the rows. After seeding, the flats were sectioned into two equal portions and 15 ml. of antidote stock solution, described above, was atomized directly into the exposed seed and soil in the open furrow in one-half of the flat. The untreated section of the flat served as an herbicide check. The seeds were covered with the one pint of soil which had been removed earlier. After four weeks the percent injury of the rice in the antidote treated half of the flat and the percent injury of the rice in the untreated half were recorded. These results reported as percent injury treated/percent injury untreated are shown in Table II.

TABLE II

HERBICIDE: ORDRAM

| Compound No. | ANTIDOTE: Rate & Method | | ANTIDOTE: Rate & Method | | % Injury W/Antidote | % Injury in Control |
| --- | --- | --- | --- | --- | --- | --- |
| 1 | 5 | IF | 4.5 | PPI | 40 | 50 |
| 2 | 5 | IF | 4.5 | PPI | 30 | 50 |
| 3 | 5 | IF | 4.5 | PPI | 50 | 50 |
| 4 | 5 | IF | 4.5 | PPI | 50 | 50 |
| 5 | 5 | IF | 4.5 | PPI | 30 | 50 |
| 6 | 5 | IF | 4.5 | PPI | 30 | 50 |
| 7 | 5 | IF | 4.5 | PPI | 30 | 50 |
| 8 | 5 | IF | 4.5 | PPI | 40 | 50 |
| 9 | 5 | IF | 4.5 | PPI | 40 | 50 |
| 10 | 5 | IF | 4.5 | PPI | 30 | 50 |
| 11 | 5 | IF | 4.5 | PPI | 40 | 50 |
| 12 | 5 | IF | 4.5 | PPI | 20 | 50 |
| 13 | 5 | IF | 4.5 | PPI | 30 | 50 |
| 14 | 5 | IF | 4.5 | PPI | 20 | 50 |

Evaluation procedures and various methods of application can be employed, such as pre-plant incorporation of (1) the herbicide and antidote separately, (2) as a tank mix with the herbicide and antidote together and (3) seed treatment with the antidote prior to planting. The application can be by incorporation, whereinafter the seeds and surrounding soil in which the herbicide is applied to the soil; and treatment of the crop seeds with an antidote candidate prior to planting in herbicide treated soil.

For tank mixes to be applied as a pre-plant incorporated application, an aliquot of herbicide stock solution was employed. Five milliliters (5 ml.) of herbicide stock solutions A or C is mixed with an aliquot of antidote candidate stock solution, such that the equivalent of a desired rate (lb/A) of herbicide and antidote, respectively, are applied and incorporated into the soil of each flat. For pre-plant incorporation, the mixed stock solutions were injected into the soil during incorporation in a 5-gallon rotary mixer.

For seed treatment, 10 grams of seed in a suitable container was shaken with an aliquot of antidote stock solution, such that the seed treatment was equivalent to a desired w/w percent. Shaking was continued until the seeds were uniformly covered.

The compositions of the present invention for the protection of cultivated crop plants comprise the active herbicidal compound and an antidote therefor selected from the above-described compounds. The compositions of herbicide and antidote can be prepared by conventional methods through the thorough mixing and grinding of the active herbicide agents and the antidote with suitable carriers and/or other distribution media, possibly with the addition of dispersion agents or solvents.

The antidote compounds and compositions of the present invention can be used in any convenient form. Thus, the antidote compounds and composition with the thiolcarbamate herbicide can be formulated into emulsifiable liquids, emulsifiable concentrates, liquid, wettable powder, powders, granular or any other convenient form such as a non-phytotoxic quantity of an herbicidal antidote compound admixed with a selected herbicide and incorporated into the soil prior to or after planting the seed. It is to be understood, however, that the herbicide can be incorporated into the soil and thereafter the antidote compound can be incorporated into the soil. Moreover, the crop seed itself can be treated with a non-phytotoxic quantity of the compound and planted into the soil which has been treated with herbicide, or untreated with the herbicide and subsequently treated with the herbicide. The addition of the antidote compound should not affect the herbicidal activity of the herbicide.

The antidote compounds and compositions of this invention can be used in any convenient form. It is preferred to use the antidote in the form of a formulation containing the antidote and an inert carrier. The herbicide can be included in the same formulation if desired. Such formulations can take the form of dusts, wettable powders, granules, solutions of emulsifiable concentrates. The antidote can be incorporated into the soil before, after or simultaneously with the herbicide. Solutions of antidote and herbicide can also be combined to form a tank mix which can be applied into the seed furrow before or after crop seed placement, prior to covering the seeds with soil. This in-furrow method economically and effectively placed the antidote immediately adjacent the crop seed to be protected from herbicidal injury. The in-furrow application, described hereinabove, can take place before or after herbicide has been applied to the soil. In yet another method, the crop seeds can be treated with the antidote prior to planting.

What is claimed is:

1. A herbicidal composition consisting essentially of the thiolcarbamate herbicide compound S-ethyl hexahydro-1H-azepine carbothioate and a non-phytotoxic antidotally effective amount of a compound having the formula

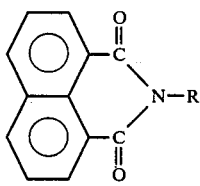

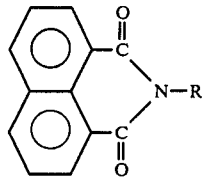

wherein R is selected from the group consisting of alkyl containing 5-20 carbon atoms, inclusive; hydroxyalkyl containing 1-6 carbon atoms, inclusive, and lower alkoxyalkyl containing 2-10 carbon atoms, inclusive; benzyl; chloroacetamido; halophenylureido, in which halo is 1-4 chloro, bromo or fluoro; thiazolyl; benzimidazolyl and halo substituted benzimidazolyl, in which halo is 1-3 chloro, bromo or fluoro.

2. The composition of claim 1 wherein R is alkyl.
3. The composition of claim 2 wherein R is i—$C_5H_9$.
4. The composition of claim 2 wherein R is n—$C_7H_{15}$.
5. The composition of claim 2 wherein R is n—$C_{11}H_{23}$.
6. The composition of claim 2 wherein R is n—$C_{16}H_{33}$.
7. The composition of claim 1 wherein R is hydroxyalkyl.
8. The composition of claim 7 wherein R is —$CH_2CH_2OH$.
9. The composition of claim 1 wherein R is lower alkoxyalkyl.
10. The composition of claim 9 wherein R is —$CH_2CH(OC_2H_5)_2$.
11. The composition of claim 1 wherein R is benzyl.
12. The composition of claim 1 wherein R is chloroacetamide.
13. The composition of claim 1 wherein R is halophenylureido.
14. The composition of claim 13 wherein R is

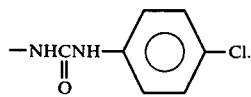

15. The composition of claim 1 wherein R is thiazolyl.
16. The composition of claim 1 wherein R is benzimidazolyl.
17. The composition of claim 1 wherein R is halo substituted benzimidazolyl.
18. The composition of claim 17 wherein R is 4-chlorobenzimidazolyl.
19. The method of protecting rice from herbicidal injury which comprises applying to the soil the herbicidal composition of claim 1.
20. A method of protecting rice from herbicidal injury which comprises treating rice seeds prior to planting with a non-phytotoxic antidotally effective amount of a compound of the formula wherein R is selected from the group consisting of alkyl containing 5-20 carbon atoms, inclusive; hydroxyalkyl containing 1-6 carbon atoms, inclusive, and lower alkoxyalkyl containing 2-10 carbon atoms, inclusive; benzyl; chloroacetamido; halophenylureido, in which halo is 1-4 chloro, bromo or fluoro; thiazolyl; benzimidazolyl and halo substituted benzimidazolyl, in which halo is 1-3 chloro, bromo or fluoro.

21. The method of claim 19 wherein R is alkyl.
22. The method of claim 21 wherein R is i—$C_5H_9$.
23. The method of claim 21 wherein R is n—$C_7H_{15}$.
24. The method of claim 21 wherein R is n—$C_{11}H_{23}$.
25. The method of claim 21 wherein R is n—$C_{16}H_{33}$.
26. The method of claim 19 wherein R is hydroxyalkyl.
27. The method of claim 26 wherein R is —$CH_2CH_2OH$.
28. The method of claim 19 wherein R is lower alkoxyalkyl.
29. The method of claim 19 wherein R is benzyl.
30. The method of claim 19 wherein R is chloroacetamide.
31. The method of claim 19 wherein R is halophenylureido.
32. The method of claim 19 wherein R is

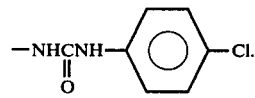

33. The method of claim 19 wherein R is thiazolyl.
34. The method of claim 19 wherein R is benzimidazolyl.
35. The method of protecting rice crop from injury, said injury due to S-ethyl hexahydro-1H-azepine carbothioate comprising applying in-furrow to the rice seed and surrounding soil containing said thiolcarbamate herbicide prior to covering and planting said rice seed, a non-phytotoxic antidotally effective amount of a compound of the formula

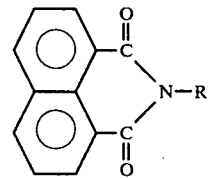

wherein R is selected from the group consisting of alkyl containing 5-20 carbon atoms, inclusive; hydroxyalkyl containing 1-6 carbon atoms, inclusive, and lower alkoxyalkyl containing 2-10 carbon atoms, inclusive; benzyl; chloroacetamido; halophenylureido, in which halo is 1-4 chloro, bromo or fluoro; thiazolyl; benzimidazolyl and halo substituted benzimidazolyl, in which halo is 1-3 chloro, bromo or fluoro.

36. The method of claim 35 wherein R is alkyl.
37. The method of claim 36 in which R is i—$C_5H_9$.
38. The method of claim 36 in which R is n—$C_7H_{15}$.
39. The method of claim 36 in which R is n—$C_{11}H_{23}$.
40. The method of claim 36 in which R is n—$C_{16}H_{33}$.
41. The method of claim 35 in which R is hydroxyalkyl.
42. The method of claim 35 in which R is lower alkoxyalkyl.
43. The method of claim 35 in which R is benzyl.
44. The method of claim 35 in which R is chloroacetamide.
45. The method of claim 35 in which R is halophenylureido.
46. The method of claim 35 in which R is

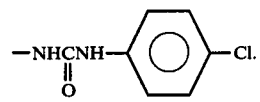

47. The method of claim 35 wherein R is thiazolyl.
48. The method of claim 35 wherein R is benzimidazolyl.
49. The method of claim 19 wherein R is halo substituted benzimidazolyl.
50. The method of claim 18 in which R is 4-chlorobenzimidazolyl.
51. The method of claim 35 wherein R is halo substituted benzimidazolyl.
52. The method of claim 51 wherein R is 4-chlorobenzimidazolyl.

* * * * *